United States Patent
Millán-Galante

(10) Patent No.: US 11,948,445 B2
(45) Date of Patent: Apr. 2, 2024

(54) SECURE PROCESSING OF ALARM MESSAGES FOR A MEDICAL DEVICE

(71) Applicant: Fresenius Medical Care Deutschland GmbH, Bad Homburg (DE)

(72) Inventor: María Millán-Galante, Bad Homburg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 922 days.

(21) Appl. No.: 16/938,813

(22) Filed: Jul. 24, 2020

(65) Prior Publication Data
US 2021/0077694 A1 Mar. 18, 2021

(30) Foreign Application Priority Data
Sep. 16, 2019 (EP) ..................................... 19197474

(51) Int. Cl.
| | |
|---|---|
| *G08B 29/02* | (2006.01) |
| *A61M 1/14* | (2006.01) |
| *G06F 9/54* | (2006.01) |
| *G08B 5/22* | (2006.01) |
| *G08B 21/18* | (2006.01) |
| *G16H 40/63* | (2018.01) |

(52) U.S. Cl.
CPC ............ *G08B 21/18* (2013.01); *A61M 1/14* (2013.01); *G06F 9/546* (2013.01); *G08B 5/22* (2013.01); *G16H 40/63* (2018.01); *A61M 2205/18* (2013.01); *A61M 2205/505* (2013.01)

(58) Field of Classification Search
USPC ...... 340/506, 517, 534, 521, 539.12, 539.22, 340/539.26, 568.2, 619, 636.18, 691.6
See application file for complete search history.

(56) References Cited

U.S. PATENT DOCUMENTS

| | | | | |
|---|---|---|---|---|
| 2013/0132977 A1* | 5/2013 | Doyle | ............... | G06F 7/50 719/318 |
| 2013/0338450 A1* | 12/2013 | Osorio | ............... | A61B 5/746 600/300 |
| 2014/0230071 A1* | 8/2014 | Adam | ............... | G16H 40/63 726/26 |

(Continued)

OTHER PUBLICATIONS

European Patent Application No. 19197474.0, Search Report (dated Mar. 4, 2020).

*Primary Examiner* — Daniel Previl
(74) *Attorney, Agent, or Firm* — Leydig, Voit & Mayer, Ltd.

(57) ABSTRACT

A medical system includes a medical device configured to provide device-related data for evaluating the reasons for an alarm in order to trigger appropriate countermeasures. The medical device includes a set of sensors, a display, and a processor. The processor is configured to generate an alarm message in response to the alarm signal provided by the set of sensors, detect a set of machine parameters in response to generating the alarm message, generate or obtain an encoded data package representing the set of detected machine parameters in a compressed format, and generate a mixed-type alarm convolute based on the alarm signal provided by the set of sensors. The alarm convolute comprises the alarm message in a readable format and the encoded data package, and the processor is configured to issue the alarm convolute on the display.

19 Claims, 4 Drawing Sheets

(56) References Cited

U.S. PATENT DOCUMENTS

| | | | |
|---|---|---|---|
| 2015/0301338 A1* | 10/2015 | Van Heugten | G09G 3/32 345/8 |
| 2015/0320314 A1* | 11/2015 | Berger | G06K 7/1417 340/870.07 |
| 2016/0011290 A1* | 1/2016 | Iannello | A61B 5/055 600/422 |

* cited by examiner

SECURE PROCESSING OF ALARM MESSAGES FOR A MEDICAL DEVICE

CROSS-REFERENCE TO RELATED APPLICATIONS

Priority is claimed to European Patent Application No. EP 19197474.0, filed on Sep. 16, 2019, the entire disclosure of which is hereby incorporated by reference herein.

FIELD

The present invention relates to the processing of alarms generated on a medical device, such as a dialysis device.

BACKGROUND

Conventional medical devices, such as hemodialysis machines, are equipped with a screen for control and operation of the device, such as a touch-sensitive screen. The screen serves for input and output of a plurality of information and messages such as alarm messages.

In clinical practice, the correct operation of the medical device is important. Therefore, in the apparatus a multiplicity of detectors (such as sensors) are installed, which detect a state of the device as needed via a message on the user interface to the user. These messages can indicate, for example, a faulty condition on the device. In case of an alarm or error message, usually an action on the device has to be carried out to transfer the faulty state back into a healthy or operating state of the machine. The alarm message may, for example in the case of a hemodialysis machine, concern an arterial blood pressure value, representing, for example, problems with the access of the bloodlines to the vascular system of the patient.

Conventionally, alarm messages are directly provided on a monitor of the medical device. This informs the nurse about the alarm state. However, in some complex situations, detailed analysis is not possible because more detailed information and data is missing.

Generally, an alarm is related to a certain state of the medical device and/or the treatment process (e.g., dialysis process). For being able to analyze the alarm situation more precisely, it would be helpful to provide machine parameters and treatment related parameters and sensor values. However, simply providing all these data on the monitor of the device is not possible because space is limited on the screen/monitor. Moreover, simply transferring the necessary data onto another machine with another (separate, additional) monitor is not possible due to security requirements as security relevant and patient-related data are involved.

SUMMARY

In an exemplary embodiment, the present invention provides a medical device. The medical device includes: a set of sensors configured to provide an alarm signal; a display; and a processor configured to: generate an alarm message in response to the alarm signal provided by the set of sensors; detect a set of machine parameters in response to generating the alarm message; generate or obtain an encoded data package representing the set of detected machine parameters in a compressed format; generate a mixed-type alarm convolute based on the alarm signal provided by the set of sensors, wherein the alarm convolute comprises the alarm message in a readable format and the encoded data package; and issue the alarm convolute on the display.

In another exemplary embodiment, the present invention provides a method for processing alarm messages issued by a medical device. The method includes: providing at least one alarm signal of a set of sensors; generating an alarm message in response to the provided at least one alarm signal of the set of sensors; in response to generating the alarm message, detecting a set of machine parameters which are related to the alarm message; and issuing, by a processor, a mixed-type alarm convolute for being displayed on a display of the medical device, wherein the alarm convolute comprises: the alarm message in a readable format; and an encoded data package representing the set of detected machine parameters in a compressed format.

In yet another exemplary embodiment, the present invention provides a system for processing alarm messages issued by a medical device. The system includes: the medical device configured to: generate an alarm message in response to an alarm signal provided by a set of sensors; detect a set of machine parameters in response to generating the alarm message; generate or obtain an encoded data package representing the set of detected machine parameters in a compressed format; generate a mixed-type alarm convolute based on the alarm signal provided by the set of sensors, wherein the alarm convolute comprises the alarm message in a readable format and the encoded data package; and issue the alarm convolute on a display; and a second device configured to: decode the encoded data package to provide decoded data; and output the decoded data.

In yet another exemplary embodiment, the present invention provides a non-transitory computer-readable medium having processor-executable instructions stored thereon for processing alarm messages issued by a medical device. The processor-executable instructions, when executed, facilitate: providing at least one alarm signal of a set of sensors; generating an alarm message in response to the provided at least one alarm signal of the set of sensors; in response to generating the alarm message, detecting a set of machine parameters which are related to the alarm message; and issuing a mixed-type alarm convolute for being displayed on a display of the medical device, wherein the alarm convolute comprises: the alarm message in a readable format; and an encoded data package representing the set of detected machine parameters in a compressed format.

BRIEF DESCRIPTION OF THE DRAWINGS

Exemplary embodiments of the present invention will be described in even greater detail below based on the exemplary figures. The invention is not limited to the exemplary embodiments. All features described and/or illustrated herein can be used alone or combined in different combinations in embodiments of the invention. Features and advantages of various embodiments of the present invention will become apparent by reading the following detailed description with reference to the attached drawings which illustrate the following.

DETAILED DESCRIPTION

Figure 1:
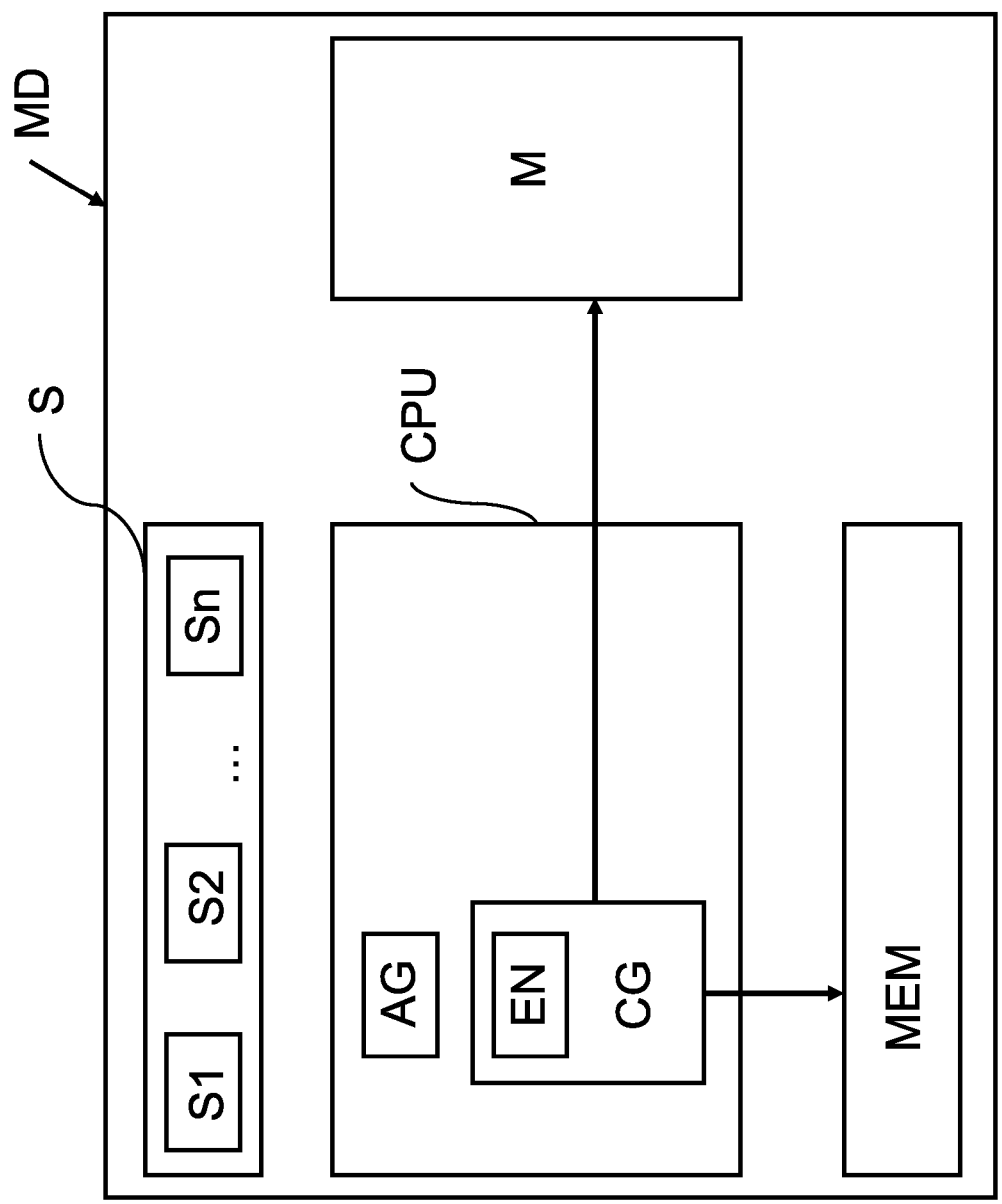
FIG. 1 is a block diagram of a medical device according to an exemplary embodiment.

Exemplary embodiments of the present invention provide relatively more device-related data for evaluating the reasons for an alarm in order to trigger appropriate counter-measures. Further, the information and data are provided in a secure manner, in particular in compliance with data protection regulations for patient-related data. Further, device-related data is provided even if the medical device is a stand-alone device without any data communication interfaces (i.e. without network interfaces).

Exemplary embodiments include a method for processing alarm messages, a medical device, a system, a computer program or a respective computer readable medium.

In an exemplary embodiment, a medical device, such as a dialysis device, includes:
a set of sensors configured to provide an alarm signal; the alarm signal may relate to the medical (treatment) device or to the patient (undergoing the treatment, such as physiological parameters) or to the technical procedure; the alarm signal may be detected or acquired parameter value or a measured value;
a display unit, such as a screen (e.g., a touch screen);
a central processing unit (CPU), with
an alarm generator configured to generate an alarm message (e.g., treatment-related or device-related) in response to at least one alarm signal provided from the set of sensors, wherein the alarm message is related to or accompanied by a set of machine parameters (such as machine parameters of the device and/or patient-related measured values during treatment with the medical device), which are detected in response to and in a time interval in which the alarm message has been generated or the alarm signal has been provided by the set of sensors;
a convolute generator configured to generate a mixed-type alarm convolute and to issue it on the display unit in case an alarm signal has been provided by the set of sensors; wherein the convolute generator comprises or accesses:
an encoder for generating an encoded data package, representing the set of detected machine parameters being provided in a second compressed format; and wherein the convolute generator is configured to generate the alarm convolute, wherein the alarm convolute may comprise:
the alarm message which is provided in a first readable format (in particular in clear text, readable format); and
the encoded data package, provided in a second compressed format (unreadable, non-legible format, machine-readable format).

Accordingly, relevant technical system data is acquired just after or in response to the alarm signal being provided. This allows for evaluation of the alarm message and for automatic calculation of counter measures. Further, the necessary information may be transferred in a secure manner to an external device, in particular even without a data link between the medical device and the external device.

In an exemplary embodiment, the encoder for generating the encoded data package is provided on the CPU. Alternatively, it may be provided on an external device in data communication with the CPU. The encoder may be operated with an encoding algorithm, in particular for generating a one- or two-dimensional binary code, such as a QR code, flicker code, barcode, etc. The algorithm may be executed on the CPU at the medical device or alternatively externally. This has the technical effect that the space required for displaying the data may be reduced significantly. Further, the data may be secured in order not to provide and transfer them as plain text.

In another exemplary embodiment, the encoded data package is or comprises a graphical code, which represents the set of detected machine parameters and which is generated by the encoder. The code is decodable by a reader, such as an optical reader (e.g., a QR or barcode reader) of a second device (e.g., smartphone and/or tablet) separate from the medical device. This makes the processing of alarm messages much more flexible as external and mobile devices may be used for error handling and/or monitoring and surveillance.

In another exemplary embodiment, the encoded data package, which is generated by the encoder, is integrated into a graphical element representing the alarm message. This allows for a correct and clear association between the encoded data package and the related alarm message. With this feature, failures due to a wrong linkage or coupling between the data may be avoided.

In another exemplary embodiment, the sensor for providing the alarm signal is located at the medical device and/or on the patient. The sensor may for example be a temperature sensor for receiving a temperature value of the dialysis fluid and/or dialysate and/or a sensor for measuring the blood pumping rate. In a further embodiment, it is configurable which sensors are to be activated and thus considered for providing the alarm messages. On a user interface, a subset of sensors may be selected for being considered for calculation of the alarm message. This allows for adapting the processing to the specific use cases.

In another exemplary embodiment, the medical device is an encapsulated unit or an enclosed device without any data communication link or network connection to any other device such as a non-networkable stand-alone device. This has the technical advantage to improve security, and in particular to improve cyber security by reducing the options for cyber-attacks.

In another exemplary embodiment, the medical device is equipped with a storage unit or a memory for storing the alarm convolute or parts thereof. The memory may be configured to store an associating data structure, such as a table with the alarm convolute. The memory may be provided in the medical device. The alarm convolute comprises the alarm message in relation to or in connection/association with the set of detected machine parameters, acquired in response to generating the alarm message.

It will be appreciated that the aforementioned features described in connection with a medical device are also applicable to other exemplary implementations of the invention, including for example a computer program or a method. In other words, the subject matter which is described with respect to the device can be improved with features described in the context of the method and vice versa. In this case, the functional features of the method are embodied by structural units of the system and vice versa, respectively. Generally, in computer science a software implementation and a corresponding hardware implementation may correspond and may be equivalent from a complexity and computational perspective (Church thesis). Thus, for example, a method step for "storing" data may be performed with a storage unit and respective instructions to write data into the storage. For the sake of avoiding redundancy, although the method may also be used in the alternative embodiments described with reference to the device, these embodiments are not explicitly described again for the method.

In another exemplary embodiment, a method for processing alarm messages issued by a medical device includes:
providing at least one alarm signal of a set of sensors;

generating an alarm message (e.g., device-related and/or treatment-related) in response to the provided at least one alarm signal of the set of sensors;

detecting a set of machine parameters, which are related to the alarm signal, in particular related with respect to a time relation and content relation (both relating to the alarm signal);

issuing a mixed-type alarm convolute by a central processing unit for being displayed on a display unit of the medical device, wherein the alarm convolute comprises the alarm message which is provided in a first readable format (e.g., clear text, readable format) and wherein the alarm convolute additionally comprises an encoded data package, representing the set of detected machine parameters in a second compressed format.

In an exemplary embodiment, detecting the set of machine parameters is executed in response to generation of the alarm message or to the providing of the at least one alarm signal. The detection may be activated and de-activated. In particular, the detection may be triggered if an alarm message was generated. This makes sure that there is always a time link between the alarm signal and the acquired machine parameters.

In another exemplary embodiment, the set of machine parameters which is to be detected is pre-configurable in a preceding configuration phase. This allows for adapting the method for alarm processing to specific use cases (e.g., a use case where only temperature related alarms are relevant and thus only temperature signals are detected).

In still another exemplary embodiment, the method further comprises the following steps, to be executed on a second device after having received the encoded data package from the medical device:

decoding the encoded data package for generating decoded data, representing the set of detected machine parameters in the first readable format; and displaying the decoded data, in particular on the second device, which is separate and usually located apart from or with distance to the medical device.

In still another exemplary embodiment, the method further comprises the following step to be executed on the second device:

executing an evaluation algorithm for providing control instructions with respect to a medical treatment on the medical device. The evaluation algorithm may be based on evaluating historical data of alarm convolutes or parts thereof (e.g., machine parameters) stored in a memory. This feature allows for a more detailed analysis and processes patterns in the acquired machine parameters, in order to learn patterns which are associated to alarm messages.

In another exemplary embodiment, the method further comprises the following step, to be executed on the second device:

executing a prioritization algorithm for prioritizing the generated decoded data, in particular for being displayed in a prioritized manner on a second display unit of the second device. This helps to locate the most relevant and important information at a topmost position.

In another exemplary embodiment, a system for processing alarm messages issued by a medical device includes:
the second device;
a decoder configured to decode the encoded data package to provide decoded data (i.e., the "original" detected machine parameters in the readable format). Thus, the decoder is configured to convert the optical data in the second compressed format into legible, in particular textual, data in an uncompressed format; and an output module configured to output the decoded data.

The decoder and/or the output module may be integrated on the second device. However, it is also possible, to provide these electronic modules in a cloud system, where the decoder and the output module are provided separately (e.g., on a server with high resources in the cloud).

In an exemplary embodiment, the decoder is activated only if a verification signal is provided. The verification signal may be received via a user input interface for receiving a license code. It is also possible to use another signal or value, received from another computing entity as the verification signal (e.g., data representing a valid authorization procedure of the user).

In another exemplary embodiment, the second device is provided with a data communication interface (e.g., to a server). With this feature, it is possible to extend the functionality of an encapsulated and non-networked medical device in a secure manner with additional features, namely with (e.g., evaluation) services rendered remotely by, for example, the second device or by a server without transferring data from the medical device outwards over a data communication link. This is possible because the alarm convolute is only transferred via an optical medium or data connection.

In still another exemplary embodiment, the output module is provided on the second device and may comprise a second display unit for displaying the set of detected machine parameters in the uncompressed format. The second device may for example be a tablet or a smartphone or another mobile device. Alternatively, the second display unit may be provided on still another entity (not the medical device and not the second device), such as a central server.

In another exemplary embodiment, a computer program includes program elements which induce a computing entity to carry out the steps of a method for processing alarm messages as described above when the program elements are loaded into a memory of computing entity.

In another exemplary embodiment, a non-transitory computer-readable medium stores program elements that can be read and executed by a computing entity in order to perform steps of a method for processing alarm messages as described above when the program elements are executed by the computing entity.

The medical device may be a technical apparatus for medical purposes. It comprises medical units and computing and/or electronic units which serve to control and operate the medical device.

In an exemplary embodiment, the medical device is a blood treatment device, such as a dialysis device. The medical device may also be an apparatus used for peritoneal dialysis or a plasmapheresis device. Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally supplied dialysis solution. The waste and toxins dialyze out of the blood through the semi-permeable membrane into the dialysis solution, which is then typically discarded. The dialysis solutions or dialysates used during hemodialysis typically contain sodium chloride and other electrolytes, such as calcium chloride or potassium chloride, a buffer substance, such as bicarbonate or acetate, and acid to establish a physiological pH, plus optionally, glucose or another osmotic agent. During treatment and thus during operation with the medical device, correct operation needs to be assured. Thus, a variety of different alarm signals may be issued in order to verify a certain state of the machine/device or to apply counter measures.

The set of sensors comprises at least one sensor for measuring physical and/or physiological data in relation to the treatment of a patient in the medical device. The set usually comprises a plurality of different types of sensors. The sensors may be temperature sensors, flow sensors, and/or pressure sensors, and the like. The sensor signals may be acquired via the sensors, and may also be acquired via reading data from memory which stores machine parameters (such as, for example, technical state information, machine/device type, operating duration, installed software, and/or energy consumption, etc.).

The display unit may be provided as a monitor integrated into the medical device. It may be a touch display. The central processing unit may comprise hardware and software components, the latter also in the form of embedded software and/or algorithms. The CPU may comprise or may be provided as a microprocessor, a field programmable gate array (FPGA) or an application-specific integrated circuit (ASIC). The CPU may serve to execute different internal functions of computing entities of the medical device. In addition to this, the CPU may further be configured to generate an alarm message and to trigger the detection of machine parameters and to issue the alarm convolute and to prepare it to be displayed on the display unit (i.e., to calculate a data set for being displayed on a monitor). The computing entities may include a processing unit, a system memory, and a system bus that connects various system components including the system memory to the processing unit. The system memory may include read-only memory (ROM) and/or random access memory (RAM). A basic input/output system (BIOS), containing basic routines that help to transfer information between elements within the personal computer, such as during start-up, may be stored in ROM. The computer may also include a memory for reading from and writing to the memory. The drives and their associated storage media or memory provide nonvolatile storage of machine-readable instructions, data structures, program modules and other data for the computer. A number of program modules may be stored on the memory, such as an operating system, one or more application programs (such as an application for executing a method for processing alarm messages and/or other program modules), and/or program data for example. A user may enter commands and information into the computer through input devices, such as a keyboard and pointing device, for example. Other input devices such as a microphone, pad, scanner, or the like may also be included. These and other input devices are often connected to the processing unit through a serial port interface coupled to the system bus. However, input devices may be connected by other interfaces, such as a parallel port or a universal serial bus (USB). A monitor (e.g., a GUI) or other type of display device may also be connected to the system bus via an interface, such as a video adapter for example, and may be integrated into the medical device.

In an exemplary embodiment, the medical device is not equipped with any data network connection to external devices and operates in an encapsulated form as a stand-alone device. Thus, no data may be transmitted via data communication links to and from other entities.

Alarm signals are received on and may be provided by the sensors or may be read from an internal memory of the device. An alarm generator, which may be implemented on the CPU is configured and specifically designed to receive these alarm signals and based thereon to generate an alarm message. In a first embodiment, it may be configured that as soon as at least one alarm signal is provided, instantaneously an alarm message will be generated directly. In a second embodiment, the alarm signals are first stored in a device internal memory together with (and thus, linked to) a time stamp.

In this second embodiment, the alarm signals (e.g., a TMP value which represents trans membrane pressure) may be aggregated and processed before issuing an alarm message (e.g., "TMP too high"). Thus, if an alarm message is generated, the CPU or a dedicated module may determine which alarm signal caused the issuance of the alarm message. Then, the memory may be accessed (look-up) in order to determine the value of the alarm signal with the respective time stamp. After having determined the time stamp, the time stamp is used for accessing the memory again for reading the machine parameters at that time (e.g., status of blood pumps). For example, several alarm signals might be necessary (temperature at a first, second and third positions via first, second and third sensors need to be received for calculating an average value) before issuing the alarm message that the temperature is above a predefined threshold. The processing of the different alarm signals to an alarm message may further in another embodiment comprise weighting the different input alarm signals. The alarm message is a digital message which is calculated and generated on the CPU based on the provided and received alarm signals. The alarm message may be provided on a user interface or on another type of output device (e.g., acoustic output). An alarm message may for example relate to "dialysate liquid rate is too low" or "TMP is too high," etc.

The machine parameters comprise two different parameters: (1) technical parameters of the medical device and (2) medical parameters, relating to the medical treatment with the device and/or to physiological data of the patient during treatment.

The technical parameters may for example relate to a hemodialysis, hemodiafiltration or peritoneal dialysis apparatus and may comprise data representing the type of the device, year of construction, serial number, software versions installed, available treatment options, blood pumping rate, a rate or temperature of dialysis fluid or dialysate, and/or transmembrane pressure (e.g., TMP). The TMP usually is decisive for a particular ultrafiltration rate and is usually regulated/controlled by the corresponding control of the extracorporeal blood circulation and dialysis or dialysis substitution fluid flows (i.e., blood pumps, dialysis fluid pump, if necessary ultrafiltration pump and substituate pump (s)). The technical parameters may further comprise a total or overall running time of the machine or medical device. This refers to the total running time of the machine, which is documented. If there is a correlation between frequently occurring alarms and a typical total running time, this may indicate a problem on the machine side (e.g., wear). The technical parameters may further comprise used disposables, such as filters, tube sets, solvent compositions, etc. The technical parameters may further comprise temperature, measured at important locations within the medical device, such as, for example, at the central processing unit, at the pumps, and the sensor casing temperature. The sensor casing temperature may be correlated to the outside temperature which may be provided via external temperatures sensors. The technical parameters may further comprise the state of the electric supply, such as a voltage value and power consumption for calculating further data, such as inlet volume in peritoneal dialysis device, dwell time of the dialysis fluid in peritoneal dialysis device, effluent volume in peritoneal dialysis device (coupled to the inlet volume), and temperature of the latter. The temperature of the effluent volume may indicate a wrong or bad temperature of the patient (e.g., being too high or too low). The effluent volume in a peritoneal dialysis device may be measured for determining the ultrafiltration volume. This parameter relates to the medical background that ultrafiltrate passes over into the peritoneum and the respective volume adds to the dialysate volume. If the dialysate remains in the peritoneum for too long, the dialysate may be resorbed via the peritoneum, which has the consequence that the patient will not be dehydrated as intended but may even receive a fluid bolus.

In another exemplary embodiment, the patient's anonymized identity may be considered as a parameter, too. This additional identity-related parameter may be used for further processing and providing mitigation data automatically. For example, for patient X, the historical (stored) data show an increased susceptibility for circulatory disorder. For this reason, an automatic mitigation measure is provided by determining a lower ultrafiltration rate combined with a longer treatment.

In an exemplary embodiment, the technical machine parameters may comprise a turbidity or clouding of the outgoing leaking dialysate. This parameter may be measured via, for example, an optical sensor and may be evaluated for detecting or recognizing pathological changes, such as peritonitis.

The medical parameters may also relate to measured values during treatment (e.g., physiological and/or medical values of the patient at the time the alarm signal has been issued or was provided, such as, for example, an accumulated ultrafiltration volume, blood pressure, and a Kt/V value (which is a number used to quantify hemodialysis and peritoneal dialysis treatment adequacy, wherein K refers to dialyzer clearance of urea, t is dialysis time and V is the volume of distribution of urea, approximately equal to a patient's total body water)). In the context of hemodialysis, Kt/V is a pseudo-dimensionless number and is dependent on the pre- and post-dialysis concentration. The Kt/V value may be determined via an online clearance measurement (OCM) method. Details of the OCM method are described in U.S. Pat. No. 5,100,554, which is incorporated herein by reference in its entirety. The patient-related machine parameters may further comprise a clearance, a body and blood temperature, pulse, EKG and/or EEG data, weight, age and origin of the patient.

Generally, the machine parameters may be measured, for example, via sensors or may be read from a storage (for example if they have been measured before or if they have to be read out from a memory module). The machine parameters may be received by the CPU and may be processed. In particular, the measured machine parameters may be checked for complying with pre-defined threshold values and/or may be validated by calculating an average value over a pre-configured period of time. Further, the measured machine parameters may be checked for correlation or may be evaluated otherwise in order to detect deficient, detrimental or adverse settings of the medical device.

In case the machine parameters are measured, the measured machine parameters are detected in response to generating the alarm message. The machine parameters may be detected at the time the alarm message is generated and—if possible—during or shortly after having provided the alarm signal. As soon as an alarm signal is detected, the detection of sensor signals is triggered immediately. This has the technical effect that there is a strong relation in time between the detection of machine parameters and the alarm signal. It is preferred that the time when the machine parameters are detected should be as close as possible to the provision of the alarm signals in order to make sure that the detected machine parameter values do correspond to the alarm signals representing an alarm state of the medical device.

The alarm convolute is a mixed-type data structure with two different parts: (1) a first part in a readable format with the alarm message and (2) a second part in a compressed format with the encoded data package.

The alarm convolute may be structured and stored in the form of a table with two respective entries. The alarm convolute is configured to be displayed on a monitor or user interface. The first format is used for displaying the alarm message, whereas the second format, being different from the first one, is used for displaying the alarm convolute. The first format comprises data in a human-readable form, whereas the second format comprises data in a coded and compressed form. The data in the second format are not human-readable (e.g., a QR code or barcode).

The convolute generator may be implemented in software and/or hardware and is configured to generate the alarm convolute. The generated alarm convolute may be provided on the display unit and/or may be stored and may be further processed. The convolute generator comprises an encoder.

The encoder may be implemented in software and/or hardware and is configured to calculate the encoded data package of the mixed-type alarm convolute. The encoder may be implemented as an optical encoder. The encoded data package is a data set, which is provided in an encoded and compressed format which is non-readable to a human, such as a one-dimensional code (e.g., barcode) or a two-dimensional code such as a matrix code (e.g., a QR code or derivatives thereof, such as a Micro-QR-Code, a secure QR code, iQR code, a frame QR code and others). For enhancing security of the transferred medical data, the encoded data package may comprise a failure correction mechanism. The display of the encoded data package requires less space than the display of the data, which are represented in the package, namely the detected machine parameters.

The encoded data package may only be readable to a decoder.

The decoder may be implemented in software and/or hardware and is configured to determine the detected machine parameters from the encoded data package and thus to convert the encoded data to decoded data. The decoder may be implemented as an optical decoder.

The encoder and the decoder are mutually dependent modules which are used for transferring and processing data (e.g., both of optical type). The evaluation algorithm is an algorithm for evaluating the decoded data of the alarm convolute. In particular, the decoded data may be compared with reference data and/or with historical data stored in a memory for providing control instructions for the control and/or operation of the medical device. Further, statistical functions may be applied in order to provide an evaluation result.

The prioritization algorithm is an algorithm for prioritizing the decoded data. This has the advantage that highly relevant messages and data are displayed first at an uppermost or top position on the display unit, which helps to reduce failures because the most important alarm messages having the highest impact may be considered and processed first.

According to another embodiment, the prioritization algorithm may be configured to prioritize not only the alarm messages as such but also the parameters related to a specific alarm message. In particular, for a specific alarm message, the parameter (regardless of whether machine-related or patient-related) is at the very top, or is highlighted, which is frequently associated with this alarm message due to the evaluation of many treatments (stored data, statistically processed). This can be numbered, so to speak, followed by the second parameter that is a second leading parameter associated with it, and so on. This makes it easier to indicate and point out the main causes. With this information, the nurse will be able to initiate the correct mitigation measures as soon as possible, which improves safety. For example, if a pressure sensor, which measures the blood pressure in the extracorporeal blood tube during hemodialysis, triggers a vacuum alarm, the pressure at this point is negative compared to the atmospheric pressure. A negative pressure being too high can result from the arterial needle sucking into the patient's blood vessel. In this case a remedial measure is lowering the blood pump rate. It is also possible, however, that the patient bends the blood tube (kinking) by changing his position. Then, a remedial measure is to rearrange the tube and avoid bends. With respect to further processing the acquired data, it is considered that certain patients may cause such kinks more frequently. Accordingly, the name of the patient (or a corresponding data set, representing the identity of the patient in anonymized form) should be placed at the top of the list. Thus, the nurse suspects that the cause is rather an action caused by the patient himself and would look for a kink instead of lowering the blood pump rate. Accordingly, unnecessarily lowering the blood pump rate (which would reduce dialysis efficiency) may be avoided.

The verification signal may refer to a license. For example, the received alarm package with the data may only be accessed and decoded (e.g., read by a user) if the second device has been verified and is allowed to do so. This improves security of the alarm processing as an additional authorization of the second device is checked before reading security relevant data concerning the alarm convolute.

Properties, features and advantages of the invention described above, as well as the manner through which they are achieved, become clearer and more understandable in the light of the following description and exemplary embodiments, which will be described in more detail in the context of the drawings. This following description does not limit the invention with regard to the disclosed embodiments. Same components or parts can be labeled with the same reference signs in different figures. In general, the figures are not drawn to scale.

Exemplary embodiments of the present invention relate to the processing of alarm messages by safeguarding security, in particular safeguarding that security relevant data (e.g., patient-related values) are not distributed over a digital network. Thus, with the present invention the risk for data security leaks are reduced or even avoided.

During operation of the medical device MD, alarm messages may be invoked which are displayed on the display unit M. However, these alarm messages are often not sufficient to analyze the reason for issuing the alarm message. For being able to analyze the reasons and circumstances, additional information may be required. This information is provided in form of machine parameters. To solve the problem, a first option would be to simply visualize the additional information with the machine parameters on the display unit M. However, the space on the display unit M is usually not sufficient to represent all the relevant machine parameters in relation to the respective alarm message. A second option would be to transfer the machine parameters to a separate entity (computer). However, usually the medical device MD is a stand-alone device without any network connections. Moreover, as security relevant data are concerned, these data cannot simply be transmitted via a network interface, if any. Exemplary embodiments of the invention address these shortcomings of conventional systems.

As can be seen in FIG. 1, a medical device MD, such as a dialysis device, is equipped with a set of sensors S, which are configured to provide alarm signals of components of the medical device or from the patient during medical treatment. Further, the medical device MD is equipped with a monitor M serving as a display unit for input and output of data relating the operation of the medical device MD. The medical device MD additionally comprises a central processing unit CPU for data processing and a memory MEM for storing data. The CPU comprises an alarm generator AG for generating an alarm message and a convolute generator CG for generating an alarm convolute, which is a two-part data structure, with alarm-related data to be displayed on the display unit M. The convolute generator CG comprises an encoder EN.

Figure 2:
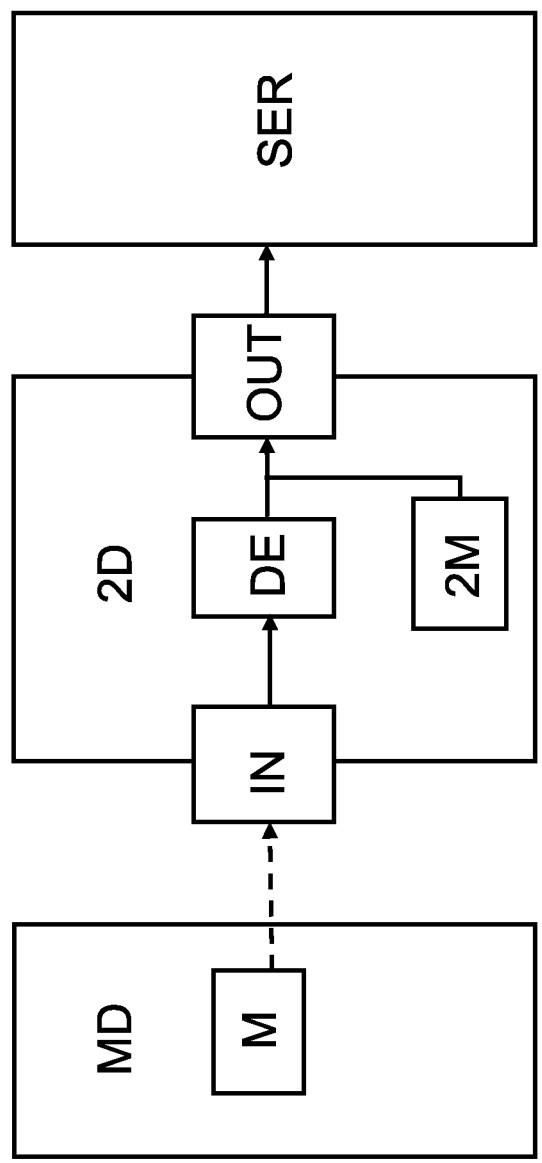
FIG. 2 is a block diagram of a system according to an exemplary embodiment.

FIG. 2 shows an exemplary system comprising a dialysis device MD, a second device 2D, and further device(s) SER. The dialysis device MD generates an encoded data package, which may, for example, be provided as or may comprise a QR code with a predetermined set of treatment data or other machine data, which may be detected by sensors S. The encoded data package is provided on the display unit M of the medical device MD. This displayed data can then be read optically via an input interface IN of a second device 2D (e.g., a mobile device). As the data are only transferred optically (no data connection), the line is dotted in FIG. 2, whereas the connection, via the output interface OUT between the second device 2D and further devices SER is a data connection. The second device 2D is equipped with a decoder DE (e.g., a QR code reader or any other reader) configured to interact with the encoder EN of the medical device MD. The QR code reader DE reads the data and may display the same on a second monitor 2M of the second device 2D and/or may transmit the data to a server SER for further processing.

Further processing on the server SER may, for example, comprise accessing a trained neural network. The trained neural network may be trained to deduce from certain states, defined by the machine parameters, which types of alarms, if any, might be caused in the future. A model may be trained which relates certain patterns of machine parameters to states of the medical device MD (correct or failure state) and in case of a failure state, a probability for a particular alarm message may be deduced. Thus, the evaluation via the trained neural network or a machine learning tool may be used to execute a kind of predictive maintenance of the medical device. All basic treatment data needed for the evaluation of the patient in the form of machine parameters may be included in the QR code and may be combined with any treatment-related alarm message, which has been triggered at the medical device MD. Thus, the alarm-related QR code would allow the nurse to have the exact values of the pre-defined machine parameters and treatment data on a display (e.g., arterial and venous pressure, TMP (transmembrane pressure), QB (blood pump rate), UF (ultrafiltration) data) corresponding to the time the alarm was triggered. There may be an integration of the QR code as an example of the encoded data package in the alarm message to allow the nurse to scan the values and to have all required data at once.

The QR code is stored together with the alarm in an internal memory MEM of the medical device MD and displayed together with the alarm on the monitor M. The memory MEM may be a specific memory serving as error memory for easier extraction of failure data and respective analysis. The invention provides the advantage that all relevant data for evaluating the alarm state are present and can be used, inter alia to generate suggestions for counter measures or corrections. Further, the alarm convolute may be transferred further from the mobile device or any other type of second device 2D to a server SER or another computing entity. This is possible because the data are transferred not in plain text, but in encoded form. This helps to safeguard privacy of the patient and his data and to secure confidentiality.

If determined and configured, the QR code or any other type of encoded data package may be displayed in a highlighted form (e.g., in a special color or bold or flashing, etc.) in order to represent a severity level of the alarm message.

A patient-specific history with a history of alarm convolutes including the alarm related QR codes may be provided in an exemplary embodiment. This feature has the advantage that a trend for each patient may be determined. For this, a history screen may be opened to see how many alarm convolutes were displayed in a session. This makes it possible to see which are the most repeated alarms in a certain period of time. For example, patients with a history of repeated lower arterial blood pressure alarms might have been developing vascular access problems, and as the nurses are rotating their workplaces (and thus the serviced medical devices MD), this situation could be overseen in conventional systems. With the feature to open an alarm convolute history with, for example, the last 12 sessions, sufficient information is provided to initiate mitigation measures.

In an exemplary embodiment, the second device 2D needs to authorize itself in order to take part in the alarm processing system. Thus, not all readers (QR code reader) are allowed to read the data. Only such devices which can provide a verification signal are allowed to process the data. The verification signal may be a flag or parameter representing a certain license. The verification signal may be checked, for example, on a central server in data communication with the second device 2D, in particular, in case the medical device is a stand-alone device without any data communication channel. In another embodiment, the medical device MD may be equipped with a secure data communication channel to the second device 2D so that the verification signal may be checked on the side and on the medical device MD. Thus, the verification signal, provided on the second device 2D may be transmitted "back" via the secure data communication channel to the medical device MD for final verification. In still another embodiment, based on a medical device MD with secure data connection, the QR code or any other type of encoded data package is encrypted and may be decrypted on the second device 2D via a unique key which is associated with and stored on the second device 2D.

Figure 3:
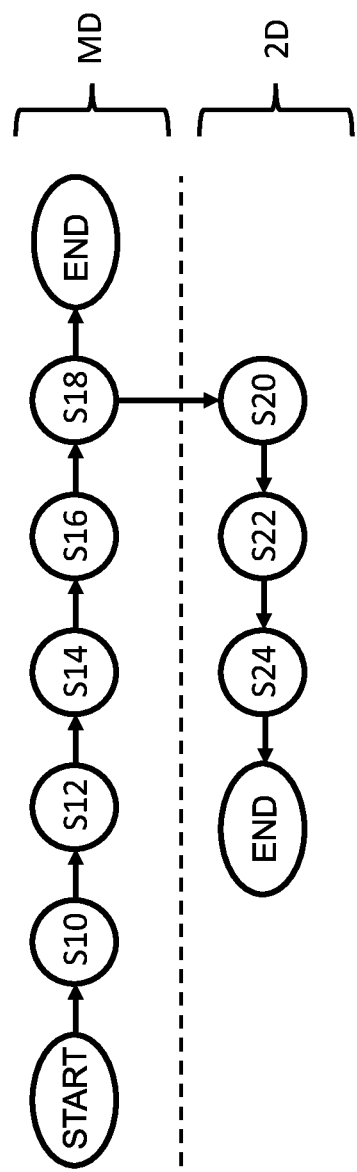
FIG. 3 is a flowchart of a first method executed on a medical device and of a second method executed on a second device according to an exemplary embodiment.

FIG. 3 shows a flowchart of a method in an exemplary embodiment. The upper part of FIG. 3 relates to steps which are executed on the medical device MD, and the lower part (below the dotted horizontal line) relates to steps which are executed on the second device 2D. After START of the method, in step S10 at least one alarm signal of the set of sensors S is provided. In step S12 an alarm message is generated in response to the provided at least one alarm signal of the set of sensors. In step S14 a set of machine parameters, which are related to the alarm message, and in particular in response to (shortly after) the generation of the alarm message, are detected. In step S16 a mixed-type alarm convolute is generated by the central processing unit CPU for being displayed in step S18 on a display unit M of the medical device MD, wherein the alarm convolute comprises the alarm message which is provided in a first readable format and wherein the alarm convolute additionally comprises an encoded data package, representing the set of detected machine parameters in a second compressed format. Then the method may switch to the steps which are carried out on the second device 2D. In step S20 the data package is received. In step S22 the encoded data package is decoded for generating decoded data, representing the set of detected machine parameters in the first readable format. After this in step S24 the decoded data are displayed on the second monitor 2M.

In an exemplary embodiment the decoded data with the detected machine parameters are displayed as a functional list. The functional list includes (graphical) user interface elements which serve to control further processing (e.g., the display of more detailed information).

In an exemplary embodiment, an evaluation algorithm may be executed. A prioritization algorithm may be executed to prioritize the displayed detected machine parameters accompanying the alarm message (e.g., highlighting important machine parameters which refer to important alarm messages).

Figure 4:
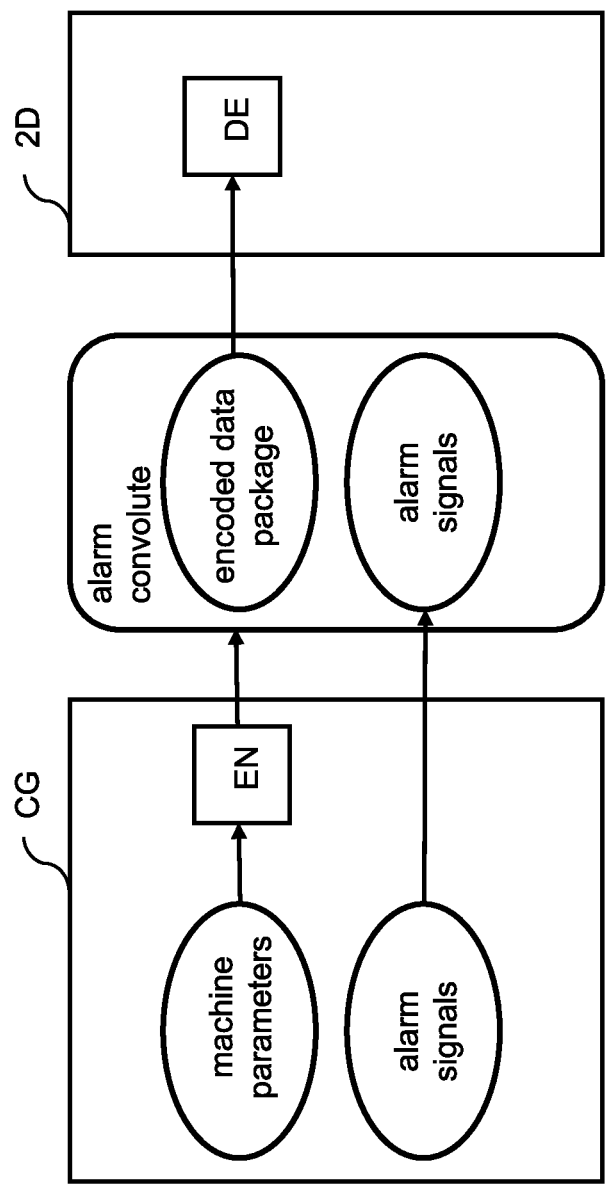
FIG. 4 is a schematic diagram of processing data for generating an alarm convolute according to an exemplary embodiment.

FIG. 4 represents the data and entities which generate the alarm convolute. The convolute generator CG comprises an encoder EN for encoding the machine parameters received at the time the alarm signal was provided or the alarm message was issued. The received alarm signals are combined with the encoded data package to generate the alarm convolute. The alarm convolute thus comprises an encoded part and a plain part. The encoded data package is configured to be decoded by the decoder DE in the second device 2D.

Other variations to the disclosed embodiments can be understood and effected by those skilled in the art in practicing the claimed invention, from a study of the drawings, the disclosure, and the appended claims. For example, the invention has been described with respect to a QR code, but other optical codes may also be used to transmit the data. Further, for a person skilled in the art, it is clear that the invention may be applied to a variety of different types of medical devices and is not limited to dialysis devices or a special type thereof. In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

Wherever not already described explicitly, individual embodiments, or their individual aspects and features, described in relation to the drawings can be combined or exchanged with one another without limiting or widening the scope of the described invention, whenever such a combination or exchange is meaningful and in the sense of this invention. Advantages which are described with respect to a particular embodiment of present invention or with respect to a particular figure are, wherever applicable, also advantages of other embodiments of the present invention.

It will be appreciated that the execution of the various machine-implemented processes and steps described herein may occur via the execution, by one or more respective processors, of processor-executable instructions stored on a tangible, non-transitory computer-readable medium, such as random access memory (RAM), read-only memory (ROM), programmable read-only memory (PROM), and/or another electronic memory mechanism. Thus, for example, operations performed by a medical device or another device as discussed herein may be carried out according to instructions stored on and/or applications installed on one or more respective computing devices.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

The invention claimed is:

1. A medical device, comprising:
a set of sensors configured to provide an alarm signal;
a display; and
a processor configured to:
generate an alarm message in response to the alarm signal provided by the set of sensors, wherein the alarm signal is linked to a time stamp;
detect a set of machine parameters corresponding to the time stamp and which relate to the alarm signal in response to generating the alarm message;
generate or obtain an encoded data package representing the set of detected machine parameters in a compressed format;
generate a mixed-type alarm convolute based on the alarm signal provided by the set of sensors, wherein the mixed-type alarm convolute comprises the alarm message in a human-readable format and the encoded data package in a non-human-readable format; and
issue the mixed-type alarm convolute on the display, wherein issuing the mixed-type alarm convolute on the display comprises displaying both the alarm message in the human-readable format and the encoded data package in the non-human-readable format.

2. The medical device according to claim 1, wherein the processor is configured to obtain the encoded data package from an external device in data communication with the processor.

3. The medical device according to claim 1, wherein the encoded data package comprises a graphical code representing the set of detected machine parameters, wherein the graphical code is decodable by a second device separate from the medical device.

4. The medical device according to claim 1, wherein the encoded data package is integrated into a graphical element representing the alarm message.

5. The medical device according to claim 1, wherein the medical device is an encapsulated, non-networked device without any data communication link or network connection.

6. The medical device according to claim 1, wherein displaying the encoded data package in the non-human-readable format comprises displaying a one-dimensional code or a two-dimensional code.

7. The medical device according to claim 6, wherein the one-dimensional code corresponds to a barcode, or the two-dimensional code corresponds to a QR code or a derivative thereof.

8. The medical device according to claim 1, wherein the processor is further configured to:
display a history of alarm convolutes for a respective patient.

9. The medical device according to claim 1, wherein the encoded data package further comprises a patient's anonymized identity.

10. A method for processing alarm messages issued by a medical device, comprising:
providing at least one alarm signal of a set of sensors;
generating an alarm message in response to the provided at least one alarm signal of the set of sensors, wherein the at least one alarm signal is linked to a time stamp;
in response to generating the alarm message, detecting a set of machine parameters corresponding to the time stamp and which are related to the alarm message; and
issuing, by a processor, a mixed-type alarm convolute for being displayed on a display of the medical device, wherein the mixed-type alarm convolute comprises: the alarm message in a human-readable format; and an encoded data package in a non-human-readable format representing the set of detected machine parameters in a compressed format;
wherein issuing the mixed-type alarm convolute for being displayed on the display comprises displaying both the alarm message in the human-readable format and the encoded data package in the non-human-readable format.

11. The method according to claim 10, wherein detecting the set of machine parameters is executed at the time the alarm message is generated and is triggered only in response to the alarm message being generated.

12. The method according to claim 10, wherein the method further comprises:
receiving, by a second device, the encoded data package;
decoding, by the second device, the encoded data package to generate decoded data representing the set of detected machine parameters in a readable format; and
displaying, by the second device, the decoded data.

13. The method according to claim 12, wherein the method further comprises:
   executing, by the second device, an evaluation algorithm for providing control instructions with respect to a medical treatment on the medical device by evaluating historical data of alarm convolutes or parts thereof stored in a memory.

14. The method according to claim 12, wherein the method further comprises:
   executing a prioritization algorithm for prioritizing the generated decoded data for display.

15. The method according to claim 14, wherein the prioritization algorithm comprises prioritization of the machine parameters which are related to each of the alarm messages based on frequency.

16. A system for processing alarm messages issued by a medical device, comprising:
   the medical device configured to:
      generate an alarm message in response to an alarm signal provided by a set of sensors, wherein the alarm signal is linked to a time stamp;
      detect a set of machine parameters corresponding to the time stamp and which relate to the alarm signal in response to generating the alarm message;
      generate or obtain an encoded data package representing the set of detected machine parameters in a compressed format;
      generate a mixed-type alarm convolute based on the alarm signal provided by the set of sensors, wherein the mixed-type alarm convolute comprises the alarm message in a human-readable format and the encoded data package in a non-human-readable format; and
      issue the mixed-type alarm convolute on a display, wherein issuing the mixed-type alarm convolute on the display comprises displaying both the alarm message in the human-readable format and the encoded data package in the non-human-readable format; and
   a second device configured to:
      decode the encoded data package to provide decoded data; and
      output the decoded data.

17. The system according to claim 16, wherein decoding the encoded data package is in response to a verification signal being provided.

18. The system according to claim 16, wherein outputting the decoded data comprises displaying the set of detected machine parameters in an uncompressed format.

19. A non-transitory computer-readable medium having processor-executable instructions stored thereon for processing alarm messages issued by a medical device, wherein the processor-executable instructions, when executed, facilitate:
   providing at least one alarm signal of a set of sensors;
   generating an alarm message in response to the provided at least one alarm signal of the set of sensors, wherein the at least one alarm signal is linked to a time stamp;
   in response to generating the alarm message, detecting a set of machine parameters corresponding to the time stamp and which are related to the alarm message; and
   issuing a mixed-type alarm convolute for being displayed on a display of the medical device, wherein the mixed-type alarm convolute comprises: the alarm message in a human-readable format; and an encoded data package in a non-human-readable format representing the set of detected machine parameters in a compressed format;
   wherein issuing the mixed-type alarm convolute for being displayed on the display comprises displaying both the alarm message in the human-readable format and the encoded data package in the non-human-readable format.

* * * * *